Figure 1:
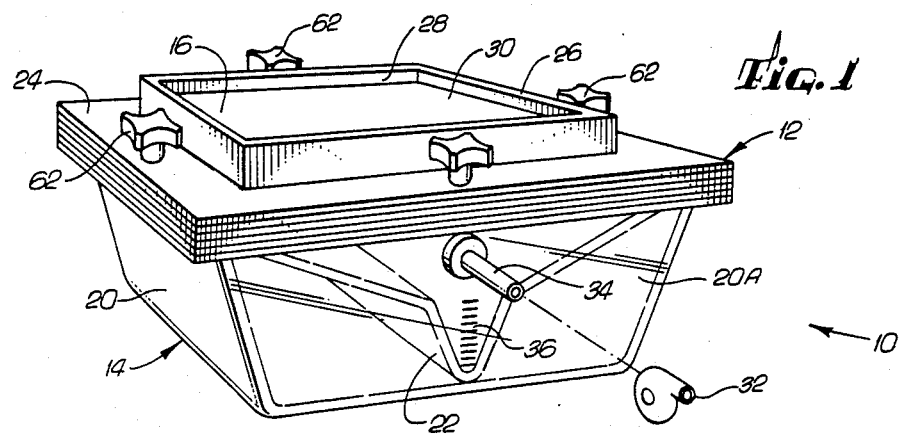

United States Patent [19]

Littlehales

[11] Patent Number: 4,818,701

[45] Date of Patent: Apr. 4, 1989

[54] APPARATUS FOR TRANSFERRING BIOLOGICAL SPECIMENS FROM A GEL TO A TRANSFER MEMBRANE AND METHOD

[75] Inventor: William J. Littlehales, Point Richmond, Calif.

[73] Assignee: American Bionetics, Inc., Hayward, Calif.

[21] Appl. No.: 49,774

[22] Filed: May 13, 1987

[51] Int. Cl.$^4$ .............................................. C12M 1/12
[52] U.S. Cl. .................................. 435/311; 435/299; 435/287
[58] Field of Search ................ 435/311, 299, 317, 284, 435/287

[56] References Cited

U.S. PATENT DOCUMENTS

| | | | |
|---|---|---|---|
| 4,296,205 | 10/1981 | Verma | 435/296 X |
| 4,598,045 | 7/1986 | Masoner et al. | 435/296 X |
| 4,603,105 | 7/1986 | Kaplan | 435/299 X |
| 4,634,676 | 1/1987 | Sapatine | 435/299 X |
| 4,726,889 | 2/1988 | Love et al. | |

FOREIGN PATENT DOCUMENTS

WO87/02132  4/1987  World Int. Prop. O.

OTHER PUBLICATIONS

"Vacuum-Blotting: A New Simple and Efficient Transfer of Proteins from Sodium Dodecyl Solfate-Polyacrylamide Gels to Nitrocellulose", M. Peferoen et al., Feds Letters, vol. 145, Nov. 2, Aug. 1982.

Detection of Methylated Sequences in Eukaryotic DNA with the Restriction Endonucleases SMAI and ZMAI, H. Youssoufian et al., *J. Mol. Biol.* (1981) 150, 133–136.

"Methylation of the Viral Genome in an In Vitro Model of Herpes Simplex Virus Latency", H. Youssoufian et al., Proc. Natl. Acad. Sci., USA, vol. 79, pp. 2207–2210, Apr. 1982.

"Restrictions Upon Epstein–Barr Virus Infection of the Leukemic Cell are Demonstrated in Patients with Hairy Cell Leukemia", T. Sairenji et al., *Hematological Oncology*, vol. 1, 251–262 (1983).

*Primary Examiner*—Larry Jones
*Attorney, Agent, or Firm*—Fulwider, Patton, Rieber, Lee & Utecht

[57] ABSTRACT

An apparatus for transferring biological specimens such as nucleic acid samples from a gel such as an agarose gel to a cooperating transfer membrane by means of a liquid transfer process is disclosed herein along with its method of use. The arrangement includes means for supporting a given gel on top of a given transfer membrane and a trough located below both. An arrangement is provided for defining a reservoir for containing a transfer liquid on top of the gel and means are also provided for causing transfer liquid contained within the reservoir to pass through the gel and transfer medium and into the trough, so as to effect a transfer of particular biological specimens carried by the gel onto the membrane. In the actual apparatus disclosed, the gel and transfer membrane are supported by an assembly of ribs and the trough includes a lowermost segment which is deeper than it is wide in cross-section, which includes graduation marks, and which is configured such that its interior is visible from outside the apparatus, whereby to be able to observe the tranfer liquid as it is being collected within the trough.

18 Claims, 2 Drawing Sheets

APPARATUS FOR TRANSFERRING BIOLOGICAL SPECIMENS FROM A GEL TO A TRANSFER MEMBRANE AND METHOD

The present invention relates generally to liquid transfer processes for transferring biological specimens such as nucleic acid samples from a gel such as agarose gel to a cooperating transfer membrane, and more particularly to a specific apparatus especially suitable for carrying out the transfer process and a specific method of using the apparatus.

There are presently acceptable techniques for transferring biological specimens such as nucleic acid samples, proteins and the like from a gel such as an agarose gel to a cooperating transferring membrane. One such technique makes this transfer electrophoretically while another one utilizes a liquid transfer process. As indicated above, the present invention relates specifically to this latter process in which a transfer liquid, commonly referred to as a buffer, is caused to move through a gel stack which includes a given gel located on top of a given transfer membrane. As the transfer liquid moves through the gel and thereafter through the transfer membrane, it carries the biological specimens to be transferred from the gel to the transfer membrane. Typically, this is carried out by means of gravitational forces only, that is, a transfer liquid is allowed to filter through the gel and transfer membrane by its own weight only. This procedure is very time-consuming.

In view of the foregoing, it is one object of the present invention to provide an apparatus especially suitable for transferring biological specimens such as nucleic acid samples from a gel such as an agarose gel to a cooperating transfer membrane by means of a liquid transfer process, and specifically an apparatus which carries out the entire transfer procedure in a relatively short period of time.

Another object of the present invention is to provide a transferring apparatus which is designed to allow the operator to visually observe the transfer liquid as it is collected after having passed through a gel and transfer membrane being acted upon, whereby to better monitor the overall process.

Still another object of the present invention is to provide a transfer apparatus designed to visually indicate accurately the amount of transfer liquid that is actually collected at any given time during the transfer process after the transfer liquid has passed through the gel and transfer membrane.

A further object of the present invention is to provide a transfer apparatus designed to reliably support the gel and transfer membrane in a reliable and yet uncomplicated way without in any way impeding the transfer process.

Still a further object of the present invention is to provide a transfer apparatus which is designed to move a specific amount of transfer fluid through the gel and transfer membrane in a specific amount of time by applying a particular pressure gradient across the gel and membrane.

Another object of the present invention is to provide a method of transferring biological specimens such as nucleic acid samples from a gel such as an agarose gel to a cooperating transfer membrane utilizing the transfer apparatus disclosed herein and in accordance with the various objects recited above.

As will be seen hereinafter, the transfer apparatus disclosed herein utilizes a base arrangement including means for supporting a gel stack, that is, a given gel on top of a given transfer membrane, so that transfer liquid can be caused to pass first through the gel and then the membrane to effect transfer of particular biological specimens from the gel to the membrane, and a trough located below the gel stack for collecting the transfer liquid after the latter has passed through the gel stack. The apparatus also includes means for causing transfer liquid to pass through the gel stack and into the trough.

In accordance with one feature of the present invention, the means for supporting the gel stack includes a porous support sheet through which the transfer liquid can flow. The transfer liquid is caused to pass through the gel stack and this support sheet by means of negative pressure applied within the trough so as to create a pressure gradient across the gel stack and support sheet. The porosity of this latter sheet and the pressure gradient are selected so that a predetermined amount of transfer liquid can be drawn through the gel stack and support sheet in a predetermined, relatively short period of time.

In accordance with another feature of the present invention, the transfer liquid is drawn through the gel stack from a reservoir which is located immediately above the gel stack. This reservoir is filled with the required amount of transfer liquid necessary. Thereafter, the previously recited pressure gradient is applied across the gel stack from the reservoir to the trough so as to cause the transfer liquid within the reservoir to be drawn downward through the gel stack and porous support sheet and eventually into the trough.

Still another feature of the present invention resides in the utilization of a collecting trough having a lowermost segment which is deeper than it is wide in cross section, whereby to define a generally V-shaped or U-shaped cross-section. At the same time, the base arrangement is configured such that the interior of the trough is visible from outside the apparatus along with graduation marks on the trough. In that way, an operator can visually observe the transfer liquid as it is collected by the trough and the amount of transfer liquid that is collected at any given point in time. Moreover, because of the shape of the trough, the amount of transfer liquid being collected can be accurately read by the graduation marks.

Yet another feature of the present invention resides in the utilization of an assembly of ribs forming part of the overall base arrangement for supporting the gel stack. This assembly of ribs supports the gel stack and porous support sheet so that these components do not sag in the presence of the previously recited pressure gradient. At the same time, the assembly of ribs preferably cooperates with the trough to add structural integrity to the latter.

Figure 2:
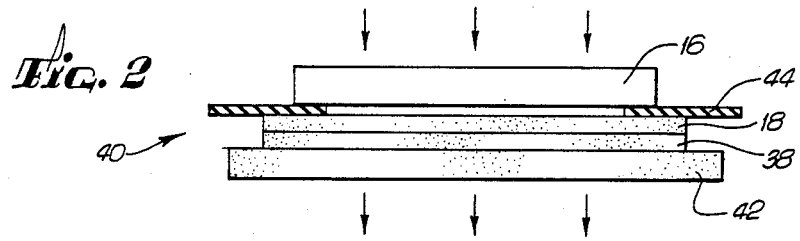
Figure 3:
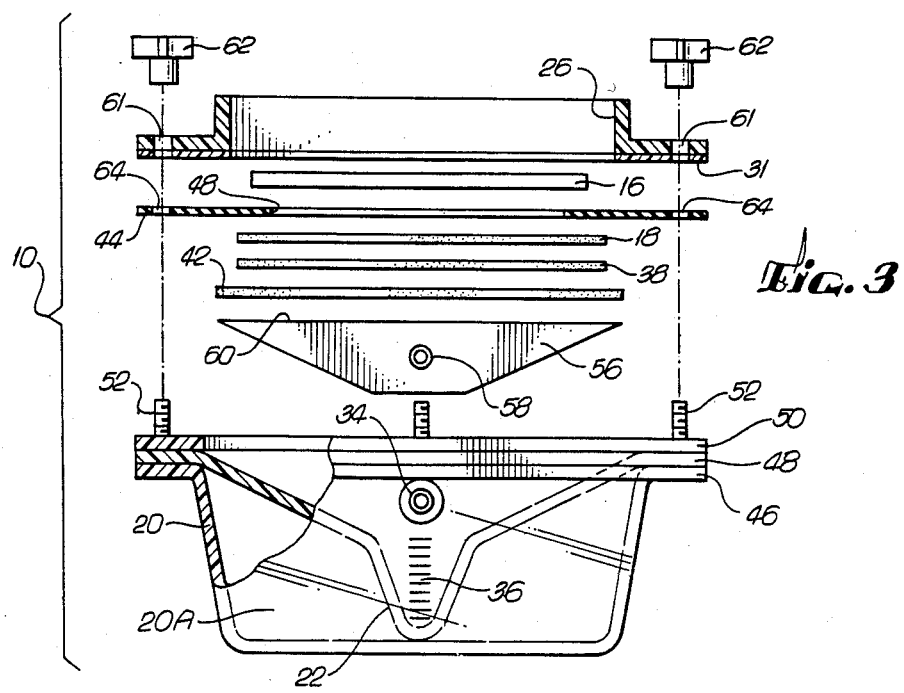
Figure 4:
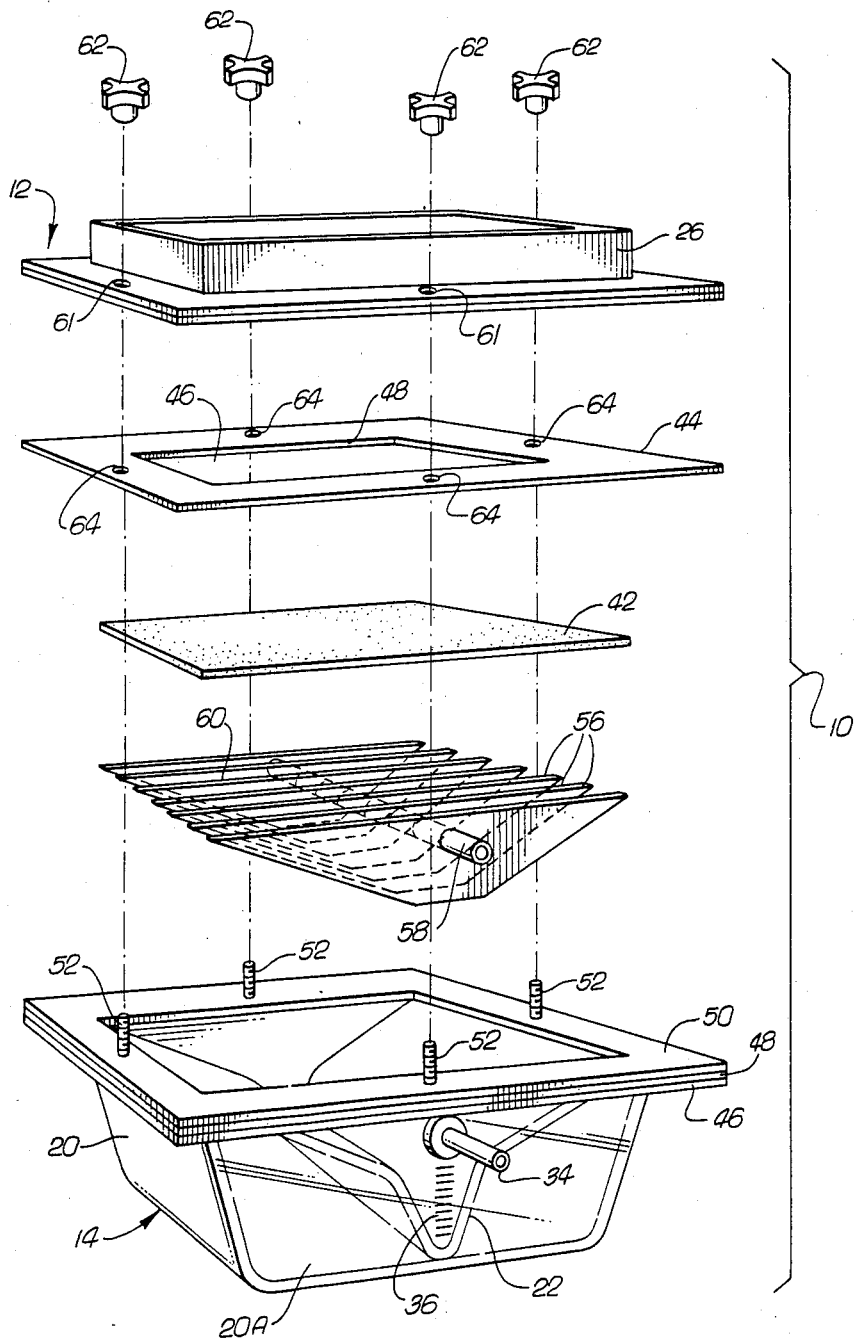

The overall apparatus and its method of operation will be described in more detail hereinafter and in conjunction with the drawings wherein:

FIG. 1 is a perspective view of an apparatus designed in accordance with the present invention for transferring biological specimens from a gel to a transfer membrane by means of a liquid transfer process;

FIG. 2 diagrammatically illustrates parts of the interior of the apparatus shown in FIG. 1;

FIG. 3 is an exploded side elevational view of the apparatus illustrated in FIG. 1 including its gel and transfer membrane; and FIG. 4 is an exploded perspective view of the apparatus illustrated in FIG. 1 without its gel and transfer membrane.

Turning now to the drawings, wherein like components are designated by like references numerals throughout the four figures, attention is first directed to FIG. 1 which illustrates an apparatus 10 which is designed in accordance with the present invention for transferring biological specimens from a gel to a cooperating transfer membrane by means of a liquid transfer process. Apparatus 10 is shown in FIG. 1 having a top arrangement 12 and a bottom or base arrangement 14 which are bolted or otherwise disengagably connected together in the manner to be described hereinafter. Base arrangement 14 includes means which will also be described hereinafter for supporting a given gel 16 on top of a given transfer membrane 18 (see FIG. 2) so that transfer liquid can be caused to pass first through the gel and then the membrane to effect a transfer of particular biological specimens, for example, nucleic acid samples, from the gel to the transfer membrane. Base arrangement 14 also includes a bottommost base housing 20 containing a trough 22 which, while not shown in FIG. 1, is located in vertical alignment below the gel and membrane for collecting the transfer liquid which is caused to pass through the latter.

Still referring to FIG. 1, top arrangement 12 is shown including a horizontally extending, outer peripheral rim 24 and an inwardly located, upstanding circumferential wall 26 which defines a reservoir 28 for containing a discrete amount of transfer liquid generally indicated at 30 on top of gel 16. Note in FIG. 1 that the top surface of gel 16 serves as the base of reservoir 28. A sealing gasket 31 (see FIGS. 3 and 4) in the form of, for example, polyurethane foam sheeting, is bonded to the underside of rim 24 and serves as a liquid seal around reservoir 28.

In actual operation, once gel 16 and membrane 18 are supported immediately above trough 22 in the manner described briefly above and the rest of the apparatus is assembled together (in the manner to be described hereinafter), reservoir 28 can be filled with a discrete amount of transfer liquid 30. Thereafter, using a vacuum pump 32 or any other suitable means, the vacuum, e.g., a negative pressure, is applied to the interior of trough 22 through a cooperating nozzle 34 sufficient to draw the transfer liquid within reservoir 28 downward through the gel 16 and membrane 18 and ultimately into trough 22 in order to effect transfer of particular biological specimens from gel 16 to membrane 18. As illustrated in FIG. 1, the interior of trough 22 can be viewed through side 20A of base housing 20 and, to this end, either the entire side 20A of housing 20 or a sufficiently large section thereof is transparent. In that way, as transfer fluid is collected within trough 22 after having passed through gel 16 and membrane 18, it can be observed from outside the apparatus through housing side 20A which serves as a viewing window. At the same time, this arrangement 14 may include suitable graduation marks 36 appropriately located, for example, on viewing window 20A, to allow a observer to actually measure the amount of transfer liquid being collected in trough 22. In this regard, as will be better seen in FIGS. 3 and 4, the trough is deeper than it is wide, in cross-section, whereby to define a generally V-shaped or U-shaped cross-section. In this way, the transfer liquid collected at any point in time during the transfer process can be more accurately measured (using the graduation marks) than would be the case if the trough were wider than it was deep, that is, generally flat. By observing the amount of transfer fluid that is collected by trough 22, the operator of apparatus 10 can determine if and when the process is complete since he knows ahead of time the approximate amount of transfer liquid required to complete the process.

A key feature of apparatus 10 is its ability to cause a predetermined amount of transfer liquid to pass through gel 16 and membrane 18 in a predetermined period of time, specifically a relatively small period of time, for example on the order of 30 minutes, as compared to prior art gravity-fed systems which require hours. The way in which this is accomplished is best illustrated in FIG. 2 in conjunction with FIG. 1. As shown in FIG. 2, gel 16 and membrane 18 and a sheet of filter paper 38 form a gel stack generally designated by the reference numeral 40 on top of a porous support sheet 42. This latter sheet forms part of an overall assembly for supporting the gel stack, which assembly, in turn, forms part of overall base arrangement 14, as will be described hereinafter.

Porous support sheet 42 is designed in conjunction with the amount of negative pressure (e.g., vacuum) applied to the interior of trough 22 in order to cause a specific amount of transfer liquid to pass through the gel stack and porous support sheet in a predetermined period of time. More specifically, it must be initially decided by the operator approximately how much transfer liquid is required to transfer particular biological specimens from gel 16 to transfer membrane 18 and the minimum amount of time this must take. For example, in an actual working embodiment, where the gel is an agarose gel approximately 0.5 cm thick and $20 \times 20$ cm in side dimensions and wherein the biological specimens are nucleic acid samples, it has been determined that approximately 90 ml of transfer liquid has to pass through the gel and membrane in at least 30 minutes. With these requirements in mind, the porosity and thickness of support sheet 42 and the amount of vacuum applied to trough 22 can be readily determined. In the actual embodiment just mentioned, the support is 0.25 inches thick, it has a porosity of 125 microns and it is constructed of polypropylene. The vacuum drawn by pump 32 in trough 22 in this same embodiment is 84 to 106 KPa (600 mm–760 mm Hg). As a result, the pressure gradient, generally indicated by the arrows in FIG. 2, is applied across gel stack 40 and porous support sheet 42. At the same time, as will be described hereinafter, apparatus 10 includes sealing means generally indicated at 44 for ensuring that transfer liquid 30 in reservoir 28 passes through the gel stack and porous support sheet as a result of the pressure gradient. The specific porosity and thickness of sheet 42 and the specific vacuum applied to the trough ensures that the desired amount of transfer liquid in the reservoir is drawn through the gel stack in the desired period of time.

It is to be understood that the description immediately above of an actual working embodiment was provided for exemplary purposes only. The present invention is not limited to the particular gel recited or the particular support sheet 42. In the actual working embodiment, the transfer membrane was constructed of nitrocellulose, 45 μm pore size and Whatmann 3 mm chromatography grade filter paper. Again, the present invention is not limited to this specific membrane or filter paper. Moreover, once the operator or technician (an individual of ordinary skill in the art) selects the particular gel to be acted upon, the biological specimens to be transferred, and the transfer membrane to receive the specimens, he can readily determine the amount of transfer liquid necessary to accomplish this in the minimum amount of time it must take. With these parameters in mind, he can readily select the appropriate porous support sheet and vacuum necessary to meet these requirements.

Referring now FIGS. 3 and 4, attention is directed to various structural details of apparatus 10. As seen in both of these latter figures, base arrangement 14 is shown including base housing 20 and trough 22 which sits within the housing. The housing includes an outer circumferential flange 46 which receives a cooperating circumferential flange 48 surrounding trough 22. A spacer flange 50 sits on top of these flanges. The three are connected together by means of four shafts having threaded end sections 52 extending up beyond the flange 50 for disengagably receiving top arrangement 12 in the manner to be described hereinafter.

As indicated previously, base arrangement 14 includes an assembly for supporting gel stack 40. This assembly not only includes the previously described porous support sheet 42 but also a rib assembly 54 which is best illustrated in FIG. 4. As seen in this latter figure the rib assembly includes a plurality of horizontally spaced, relatively thin vertically extending ribs 56 which are mounted on a common centrally located support rod 58. The ribs are generally triangular in shape so as to fit directly over trough 22 while defining a horizontally extending planar support surface 60 (see FIG. 3) upon which porous support sheet 42 sits. In this way, the ribs prevent the porous sheet and gel stack 40 from buckling as a result of the pressure gradient described in conjunction with FIG. 2. At the same time, the rib assembly allows the transfer liquid to pass therethrough from the gel stack and porous support sheet and into trough 36. Moreover, the other side of each rib 56 engages trough 22 so as to add structural integrity to the latter. That is, the ribs reinforce the trough so as to prevent the latter from collapsing inward due to the presence of negative pressure therein.

Still referring to FIGS. 3 and 4 in conjunction with FIG. 1, top arrangement 12 is shown in FIGS. 3 and 4 including the previously described rim 24 having sealing gasket 31 on its underside and upstanding side wall 26 defining reservoir 28. The rim is shown best in FIG. 4 including four through-holes 61 which receive threaded shaft sections 52 and rim 24 is positioned against spacer flange 50. Knobs 62 are then threaded over threaded shaft sections 52 in order to disengagably secure top arrangement 12 to base arrangement 14.

As stated previously, overall apparatus 10 includes sealing means 44 (FIG. 2) for ensuring that transfer liquid passes through gel stack 40 during the transferring process of apparatus 10. As illustrated in FIGS. 3 and 4, this sealing means is in the form of a rubber gasket sheet. The outer periphery of the sheet is configured so as to lie between spacer flange 50 and rim 24. To this end, the rubber gasket sheet includes four through-holes 64 for accommodating threaded shaft sections 52. The interior of rubber gasket sheet 44 includes a cutout 46 corresponding in shape to and slightly smaller than gel 16 and membrane 18. Thus, the inner circumferential edge 48 of the gasket sheet defining cutout 46 extends slightly into and between gel 16 and membrane 18 when the gasket sheet is positioned in the manner illustrated in FIGS. 2, 3 and 4. The cutout 46 allows the gel and membrane to engage one another while the gasket itself ensures that transfer liquid moves along the desired path. While the gasket has been described as being constructed of rubber, it may be constructed of any suitable material. In an actual working embodiment it is approximately 0.25 inches thick, although this could vary to a limited degree also so long as it performs its intended function.

Having described apparatus 10 structurally and functionally, attention is now directed to an overall operational description of an actual working apparatus intended for use by an actual operator. Before the apparatus is actually used, the operator should check to make sure that a sufficient vacuum can be achieved. This can be done by initially placing an uncut gasket sheet on top of porous support sheet 42. Thereafter, the top arrangement 12 is secured to the base arrangement by means of knobs 62 which are preferably tightened just enough to create a seal. Thereafter, a vacuum is supplied by means of pump 32 to a level of about 24 to 30 torr. After this procedure has been carried out, the filter paper 38 and transfer membrane 18 are cut to the size of gel 16 and preferably wet with deionized water. Thereafter, the filter paper and membrane are placed on the porous support sheet and cutout 46 is provided in gasket sheet 44. As indicated above, the cutout must be slightly smaller than the gel and transfer membrane. Preferably it is approximately 0.5 cm smaller around each edge than the gel. The gasket sheet is preferably wet with deionized water along with the filter paper and transfer membrane. After that, the gasket is positioned in the manner described previously and top arrangement 12 is again reassembled to the base arrangement.

Once the apparatus 10 is assembled in the manner described immediately above, reservoir 28 is filled with transfer liquid 30, for example 20×SSC. Thereafter, the desired vacuum is applied to trough 22, for example 24 to 30 torr. As a result of this vacuum, the gasket sheet will tightly adhere to the porous support sheet. The transferred buffer (liquid) will drip down into the collection trough through the gel stack. The amount of buffer collected varies depending on the size of cutout 46. Referring to Table 1 below, the amount of volume that should be collected for a particular window size is shown. The graduation marks 36 associated with the trough 22 can be used to monitor the completion of the transfer. The larger the size of window, the more buffer will be collected. The time required to complete a transfer will vary depending upon the percentage and thickness of the gel and the vacuum applied. For a typical 1% gel, 0.5 cm thick at 24 torr, the process will be complete in 30 minutes.

TABLE 1

| Window Size and Volume of Buffer Collected | |
|---|---|
| Window Size (cm2) | Volume Collected (ml) |
| 50 | 22 |
| 75 | 29 |
| 100 | 35 |
| 125 | 40 |
| 150 | 46 |
| 175 | 51 |
| 200 | 56 |
| 225 | 60 |
| 250 | 65 |
| 275 | 69 |
| 300 | 73 |
| 325 | 78 |
| 350 | 82 |
| 375 | 86 |

TABLE 1-continued

| Window Size and Volume of Buffer Collected | |
|---|---|
| Window Size (cm2) | Volume Collected (ml) |
| 400 | 90 |

*data obtained using λ HindIII-digested DNA on 1% agarose gel, 0.5 cm thick, at 460 mm Hg.
NOTE: Volume collected will vary ±5 ml.

It is to be understood that the foregoing operational description immediately above and Table 1 have been provided for exemplary purposes only. Neither the description nor the Table are intended to limit the present invention.

What is claimed is:

1. An apparatus for transferring biological specimens from a gel to a transfer membrane by means of liquid transfer comprising:
   (a) means to support a gel containing biological specimens on top of a transfer membrane;
   (b) means disposed above the support means to define a reservoir for transfer liquid above the gel;
   (c) means adapted to be connected to a vacuum source to cause the passage of transfer liquid from the reservoir through the gel and membrane to thereby transfer the biological specimens from the gel to the transfer membrane, including sealing means disposed between the reservoir means and the support means having an area of liquid passage therethrough smaller than the area of gel placed thereabove to thereby ensure passage of the transfer liquid through the gel; and
   (d) a trough located beneath the gel and transfer membrane to collect the transfer liquid which passes through the gel and transfer membrane to facilitate determination of the amount of transfer liquid which passes therethrough.

2. An apparatus according to claim 1 wherein said means for supporting said gel and transfer membrane includes an assembly of spaced-apart ribs located under and extending across said gel and transfer membrane for supporting both above said trough while allowing transfer liquid passing through the gel and membrane to pass into the trough.

3. An apparatus according to claim 2 wherein said supporting means includes a support sheet located on top of said ribs and under said transfer membrane, said support sheet being sufficiently porous to allow said transfer liquid to pass therethrough.

4. An apparatus according to claim 3 wherein said porous support sheet is formed of polypropylene.

5. An apparatus according to claim 2 wherein said assembly of ribs engages said trough.

6. The apparatus of claim 2 wherein the ribs have inverted trapazoidal shapes which conform in part to the upper surface of the trough.

7. The apparatus of claim 1 wherein the trough defines at least in part a sealed chamber beneath the support means.

8. The apparatus of claim 1 including means to apply a vacuum to the sealed chamber beneath the support means to cause the passage of transfer liquid from the reservoir through the gel and the transfer membrane.

9. The apparatus of claim 1 wherein the trough includes an elongated well for liquid collection in the lowermost portion thereof.

10. An apparatus according to claim 9 wherein said well in the lowermost portion is deeper than it is wide in cross-section and has a generally V-shaped or U-shaped cross-section.

11. An apparatus according to claim 10 wherein the well is sufficiently transparent to allow an operator to determine the amount of transfer liquid contained therein.

12. An apparatus according to claim 11 wherein the well includes graduation marks which facilitate determining the amount of transfer liquid contained within the well.

13. An apparatus according to claim 1 wherein said means defining the reservoir includes an annular lid having a downwardly facing, horizontally extending rim for connection with said support means and a vertically extending circumferential wall means for defining the horizontal extent of said reservoir and wherein said apparatus includes means for connecting said rim to said support means.

14. An apparatus according to claim 1 wherein said means defining the reservoir includes a lid having a downwardly facing outer rim, wherein said support means includes an upwardly facing rim in confronting relationship with the rim of said lid, wherein said seal providing means includes a sheet shaped sealing gasket having its outer periphery disposed between said confronting rims and an interior cut out corresponding in shape to but slightly smaller than said gel and membrane with the interior periphery of the gasket defining said cut out being disposed between and around the outer peripheries of the gel and membrane, and wherein said apparatus includes means for disengagably squeezing said confronting rims together.

15. A method of transferring biological specimens from a gel to a transfer membrane, said method comprising the steps of:
   (a) supporting a gel having biological specimens on top of a transfer membrane;
   (b) maintaining a reservoir of transfer liquid above the gel;
   (c) sealing the underside of the outer perimeter of the gel to prevent bypass of transfer liquid therearound;
   (d) passing transfer liquid from the reservoir first through the gel and then the membrane to effect a transfer of biological specimens carried by the gel onto the membrane; and
   (e) collecting transfer liquid which has passed through the gel and membrane in a trough beneath the gel and the membrane to determine the amount of transfer liquid which has passed therethrough.

16. The method according to claim 15 wherein a predetermined amount of transfer liquid is passed through said gel and membrane in a predetermined amount of time so as to ensure the complete transfer of the biological specimens from said gel to said membrane in as short a time period as possible.

17. The method of claim 16 wherein a predetermined vacuum is generated under the transfer membrane to cause a predetermined amount of said transfer liquid to be drawn through said gel and membrane in a predetermined period of time by said vacuum.

18. The method according to claim 17 wherein said predetermined amount of liquid is approximately 250 ml and said predetermined amount of time is about 30 minutes.

* * * * *